United States Patent [19]

Williams

[11] Patent Number: Plant 7,454

[45] Date of Patent: Feb. 26, 1991

[54] MINIATURE ROSE PLANT NAMED 'MICHOME'

[76] Inventor: Michael C. Williams, P.O. Box 203, Cross Hill, S.C. 29332

[21] Appl. No.: 459,468

[22] Filed: Jan. 2, 1990

[51] Int. Cl.[5] ..... A01H 5/00

[52] U.S. Cl. ..... Plt./9

[58] Field of Search ..... Plt. 9

*Primary Examiner*—James R. Feyrer

[57] ABSTRACT

A new and distinct variety of miniature rose plant characterized by (1) bright rose pink buds and blooms with a lighter rose pink reverse and (2) a vigorous, compact plant with abundant glossy green foliage.

1 Drawing Sheet

The present invention relates to a new and distinct variety of rose plant of the miniature rose class, which was originated by my crossing as seed parent the floribunda known as Tiki and a miniature rose Party Girl (U.S. Plant Pat. No. 4,598) as pollen parent.

Among the novel characteristics possessed by this new variety which distinguishes it from its parents and all other varieties of which I am aware are (1)high-centered blooms of rose to rose pink with rose to blush pink reverse coloring, (2) an abundance of bloom with flowers usually borne singly, (3) a slight fruity fragrance, (4) a well proportioned plant which is vigorous and shows off its blooms well against its dark green glossy foliage, and (5) a plant which grows well both in the greenhouse and outdoors, is good for growing in pots, and provides excellent garden decoration as well as cut flowers.

The present variety of miniature rose was originated by me in Laurens County, S.C. Carefully controlled conditions and aseuxal reproduction by cuttings of the new variety as performed by me in Laurens County, S.C., show that the foregoing and other distinguishing characteristics come true to form and are established and transmitted through succeeding propagations.

The accompanying photograph shows typical specimens of the vegetative growth and flowers of the new variety in different stages of development and as depicted in color as nearly true as it is reasonably possible to make the same in a color photograph of this character.

The following is a detailed description of my new rose variety, with color terminology in accordance with Exotica Horticultural Color Guide except where common dictionary terms of color definition are employed.

Type: Hardy, dwarf, upright, seedling, greenhouse, outdoors, cut flowers, garden decoration, potted plant Class: Miniature.

International Identifications:

*Variety.*—Michome.

*commercial synonym:*—Homecoming.

THE FLOWER

Observations were made from specimens grown outdoors in Laurens County, S.C., U.S.A. during the summer of 1989.

Type: Miniature.

Blooming habit: Recurrent.

Bud:

*Size.*—Medium for miniature.

*Form.*—Pear-shaped.

*Color.*—When sepals first divide: Rose (#38) at peak of bud, Blush pink (#36) at base. When petals begin to unfurl: Inside: Rose (#38) with a blend of rose pink (190 37). Outside: Petal edges rose (#38) to blush pink (#36) at base. When half-blown: Inside: Center petals rose (#38). Outer petals rose pink (#37) at petal edges. Very light blush pink (#36) from just inside edge all the way to base of petals. Reverse side of petals: Light rose (#38) at petal edge to blush pink (#36) at base.

*Sepals.*—As long as the bud, thin, pointed, ovate acuminate.

*Peduncle.*—Average length 1", smooth, erect and stable, light green color

Bloom:

*Size.*—$1\frac{1}{2}$" to $1\frac{3}{4}$" when fully expanded.

*Borne.*—Singly. Occasionally there may be one or two sidebuds.

*Form.*—High centered.

*Petalage.*—About 35.

*Color.*—During first two days: Inner petals at center of flower: rose (#38). Outer petals: rose pink (#37). Base of petals (point of attachment): Light blush pink (#36). Reverse of petals: Rose pink (#37). General tonality from a distance: Light rose (#38).

*Color change.*—Rose pink (#38) lightens to light blush pink (#36). General tonality: light blush pink (#36). After three or more days: Very light blush pink (#36).

Petals:

*Texture.*—Thick.

*Appearance.*—Inside: slightly velvety; Outside: slightly satiny.

*Form.*—Oval — First two rows become quilled, remainder are more reflexed.

*Arrangement.*—Regularly arranged.

*Petaloids in center.*—5 to 8.

*Persistence.*—Whole bloom and peduncle fall off when spent.

*Fragrance.*—Slight fruity fragrance.

*Lasting quality.*—Slow opening on plant, keeps long in refrigerator, good as cut flower.

REPRODUCTIVE ORGANS

Stamens, filaments and anthers:

*Arrangement.*—Bunched tightly around styles.

*Color.*—Yellow.
Pollen: Yellow.
Styles: Even 3/16" length, thin, tightly bunched.
Stigmas:
*Color.*—Pale green.
Hips: None.

PLANT

Form: Upright.
Growth: Vigorous and uniform branching.
*Height attained.*—20" to 26".
Foliage: Mostly 5 leaflets.
Size: Medium for miniature.
Quantity: Abundant.
Color:
*New foliage.*—Upper side: Dark green with red edges and veins. Under side: lighter shade of green with red edges and veins.
*Old foliage.*—Upper side: Dark semi-glossy green. Under side: Flat green and lighter than upper side.
Shape: Oval, pointed.
Texture:
*Upper side.*—Smooth, healthy appearance.
*Under side.*—raised veins.
Edge: Serrated.
Leaf stem:
*Color.*—Green. Under side: Paler green.

Stipules: Medium, ¼" pointed
Disease resistance: Blackspot, good: Mildew, good; Rust, good.
Wood:
*New wood.*—Color: Light green, Bark: smooth.
*Old wood.*—Color: Light green, Bark: smooth.
Thorns:
*Quantity.*—Several on main cane, with few on laterals.
*Form.*—Needle shaped with expanded base.
*Length.*—Short, ¼".
*Color when young.*—Red.
*Position.*—Irregular.
Prickles:
*Quantity.*—Very few on main canes or on laterals
Winter hardiness: Needs some protection at 10 degrees or lower. Can use mound of dirt or leaves.

I claim:

1. A new and distinct variety of rose plant of the miniature rose class, substantially as herein shown and described, characterized particularly by high-centered blooms of light rose pink coloring, with firm, thick petals, borne freely on an upright plant with glossy dark green new foliage and semi-glossy darker green old foliage, said plant being easy to propagate from cuttings, and said blooms being long-lasting on the plant and as cut flowers.

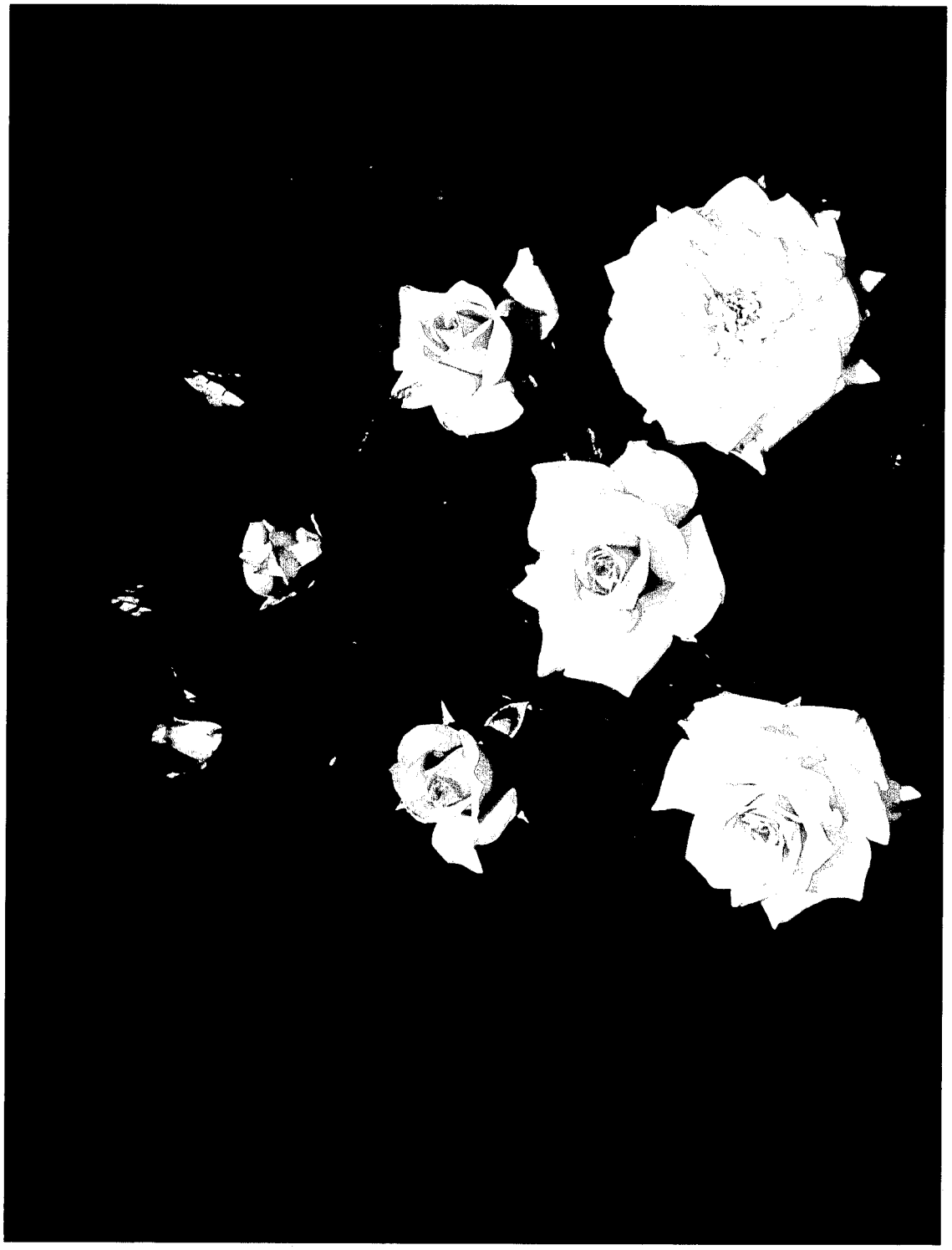

* * * * *